United States Patent [19]

Gottlieb et al.

[11] Patent Number: 4,704,497

[45] Date of Patent: Nov. 3, 1987

[54] METHOD FOR DEHYDROGENATING HYDROCARBONS

[75] Inventors: Klaus Gottlieb, Herdecke; Wilfried Graf, Dorsten; Heinz-Kuno Schadlich, Essen, all of Fed. Rep. of Germany

[73] Assignee: Veba Oel AG, Gelsenkirchen, Fed. Rep. of Germany

[21] Appl. No.: 883,426

[22] Filed: Jul. 14, 1986

Related U.S. Application Data

[63] Continuation of Ser. No. 706,835, Feb. 28, 1985, abandoned.

[30] Foreign Application Priority Data

May 5, 1984 [DE] Fed. Rep. of Germany ....... 3416672

[51] Int. Cl.$^4$ ............................................. C07C 5/02
[52] U.S. Cl. .................................... 585/654; 502/38; 502/40; 502/47; 585/616
[58] Field of Search .............. 585/654, 657, 658, 662, 585/663, 600, 616; 502/47, 40, 38

[56] References Cited

U.S. PATENT DOCUMENTS 2,831,041  4/1958  Sieg et al. ........................... 585/658
4,313,848  2/1982  Scott .................................... 502/47

FOREIGN PATENT DOCUMENTS 508155  12/1954  Canada ................................. 502/47

Primary Examiner—Asok Pal
Attorney, Agent, or Firm—Oblon, Fisher, Spivak, McClelland, & Maier

[57] ABSTRACT

A process for dehydrogenating saturated or unsaturated hydrocarbons wherein the flow direction of the oxygen-containing gas, employed for removing coke deposits on the catalyst surface, is opposite to that for the hydrocarbon feed undergoing dehydrogenation.

8 Claims, 1 Drawing Figure

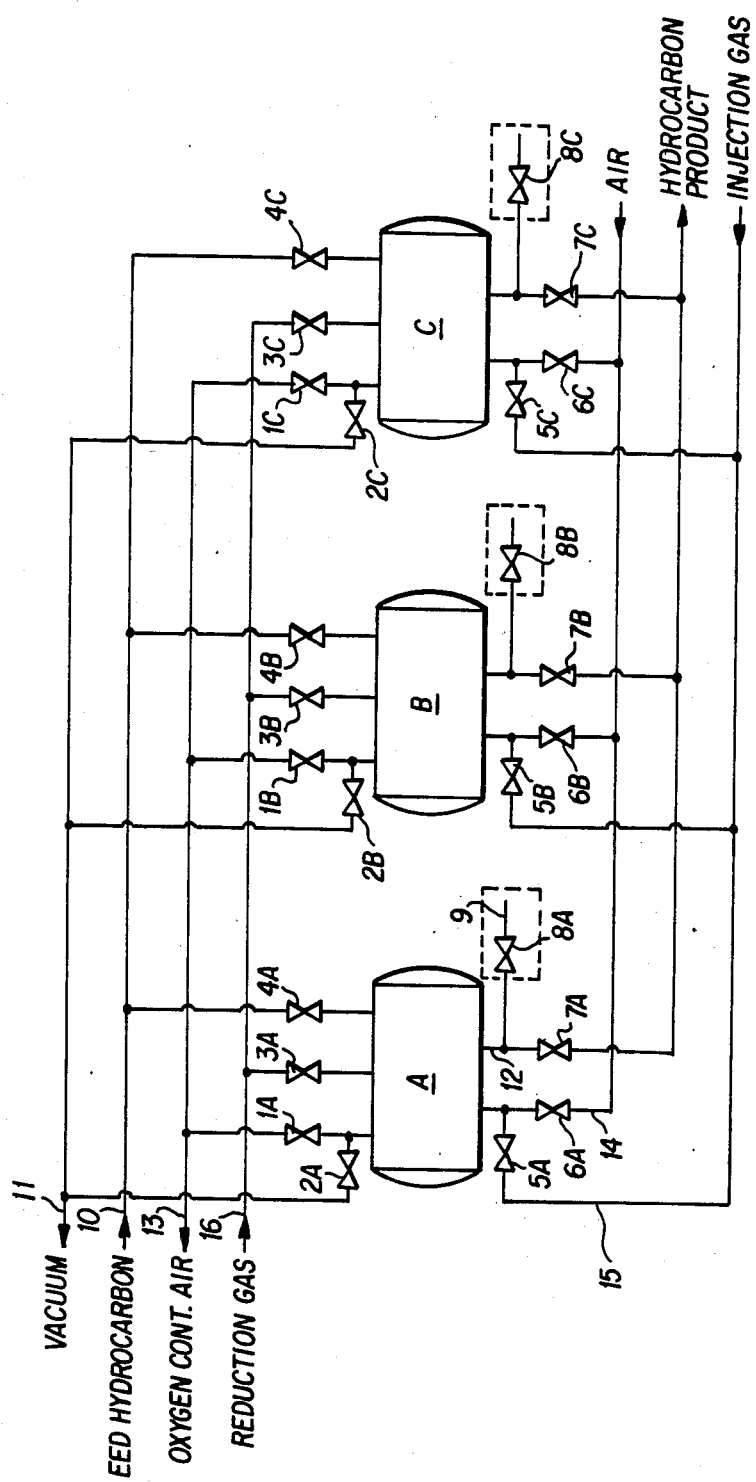

METHOD FOR DEHYDROGENATING HYDROCARBONS

This application is a continuation, of application Ser. No. 706,835, filed Feb. 28, 1985, now abandoned.

BACKGROUND OF THE INVENTION

1. Field of the Invention

This invention relates to a process for the production of unsaturated and polyunsaturated hydrocarbons from saturated and monounsaturated hydrocarbons, respectively, and contains two essential phases: a dehydrogenation phase, wherein the hydrocarbons are adiabatically passed through a fixed catalyst bed, and a catalyst regeneration phase, wherein the catalyst is regenerated by passing an oxygen-containing gas through the fixed bed. This two-phase process is characterized by a counterflow arrangement wherein the flow direction of the oxygen-containing gas in the regeneration phase is opposite that of the hydrocarbon feedstock in the dehydrogenation phase.

2. Description of the Prior Art

It has long been recognized that coke is deposited onto the surface of the catalyst during the dehydrogenation process. As a result, active sites on the catalyst needed for the dehydrogenation reaction to proceed are blocked. To restore catalytic activity, the coke is characteristically removed from the surface of the catalyst by combusting it in the presence of an oxygen-containing gas. Accordingly, a cyclical operation is established wherein the dehydrogenation phase of the hydrocarbons alternates with the regeneration phase of the catalyst. These phases are characteristically interrupted long enough to purge the catalyst free of hydrocarbons. This purging stage is normally conducted under inert gases. Dehydrogenation processes of this type are more fully described in U.S. Pat. Nos. 3,647,909, 3,711,569, 3,781,376, 4,012,335, and 4,371,730.

Dehydrogenation of the unsaturated product is a problem often encountered in such prior art processes. In the dehydrogenation phase, the hydrocarbons are contacted with the catalyst at temperatures between 500° to 650° C. Dehydrogenation typically occurs within several minutes to one hour, depending on the reaction conditions. During the reaction period, the hydrocarbon conversion diminishs continuously, what is attributed to (1) a reduction in the activity of the catalyst due to the deposition of coke on the catalytic surface and (2) the cooling of the catalyst bed by the reaction itself. This latter effect is attributable to the fact that the quantity of heat withdrawn from the catalyst bed by the endothermic dehydrogenation reaction is greater than that which can be supplied by the stream of hydrocarbons.

When the amount of coke deposited on the surface of the catalyst is small, insufficient heat is generated during the regeneration phase to replace the heat consumed by the endothermic dehydrogenation reaction. As a result, the fixed catalyst bed is not completely heated to the requisite temperature for dehydrogenation to effectively proceed. To compensate for this deficiency, the oxygen-containing gas, employed in the regeneration phase, is preheated to 600°-700° C. and is passed through the catalyst bed longer than is necessary to merely oxidize the coke.

A technique described in the above cited U.S. patents and employed in a number of industrial installations is to add gaseous or liquid fuel equivalent to the amount of heat desired to the oxygen-containing gas before it enters the reactor. This fuel is commonly referred to as "injection fuel" and is burned in the catalyst space. Such injection fuel produces the additional heat needed to reheat the catalyst bed.

In the prior art processes, the oxygen-containing gas passes through the reactor during the regeneration phase in the same direction as the hydrocarbon feed mixture undergoing dehydrogenation. In other words, the hydrocarbon and the oxygen-containing gas enter the catalyst bed at different times but at the same location. During its passage through the catalyst bed, the regeneration gas is subsequently cooled. Since the available time for the regeneration phase is limited, a steady state is not established within the bed. A somewhat steep temperature drop develops therefore in the catalyst bed toward the end of the reactor. Since the amount of dehydrogenated hydrocarbon produced decreases at lower temperatures, such decreasing temperature profiles effect the amount of product being produced. Further, since at the beginning of the reaction phase the freshly regenerated catalyst is very active, reduced temperatures have a severe disadvantageous effect upon the yield.

The prior art processes are further disadvantageous over the present invention since they are accompanied by cracking reactions. Such reactions are attributed to heating the hydrocarbon fuel mixture at high temperatures prior to feeding them into the reactor.

German OS No. 23 04 280 discloses a sulfide recovery process employing a counterflow arrangement. In this process, a bauxite catalyst is employed in the production of elementary sulfur which, in turn, is produced by partially combusting a hydrogen sulfide stream with air. Upon the bauxite catalyst, coke-like particles are deposited. These deposits are removed from the catalyst by burning the catalyst with molecular oxygen in the presence of an inert gas. The regeneration gas is then passed in the flow direction opposite to that employed for normal operation of the sulfur recovery unit. In such sulfide recovery processes, substantial quantities of liquid sulfur residues remain in the conversion zone and are not driven off by the purge gas. They can be removed by the physical action of the stream of the regeneration materials. The conditions, purpose and effect of passing the regeneration gas stream in the counterflow direction to that of the reaction gas stream radically differ in such sulfur recovery processes compared to the dehydrogenation process of this invention.

SUMMARY OF THE INVENTION

Accordingly, it is an object of this invention to reduce the input of energy required for the dehydrogenation of hydrocarbons, thereby rendering a more economically feasible dehydrogenation process.

It is also an object of this invention to provide a cost effective dehydrogenation process wherein the costs for purifying the resulting dehydrogenated products are substantially reduced.

Further, it is also an object of this invention to provide a dehydrogenation process which circumvents the disadvantages normally encountered in the prior art processes. In particular, it is an object of this invention to suppress the undesired cracking of hydrocarbons.

According to the present invention, the foregoing and other objects are attained by providing a dehydrogenation process wherein the oxygen containing gas in the regeneration phase is passed in the catalyst bed in a direction opposite to that of the hydrocarbon feed flow in the dehydrogenation phase. As a result, during the regeneration phase a temperature profile is produced in the fixed catalyst bed wherein the temperature increases in the flow direction of the hydrocarbons which are to be dehydrogenated. Further, according to this invention, the reaction temperature is maintained at satisfactory levels without heating the hydrocarbon feed mixture to excessive temperatures prior to feeding the feedstock into the reactor. As a result, cracking reactions of the hydrocarbons are minimized. Accordingly, the selectivity of the process for the desired olefinic reaction product is increased.

Further, according to this invention, the dehydrogenated products produced by this process are cheaper to purify than those products produced by the processes of the prior art. Under the countercurrent conditions of this invention, a greater amount of the feedstock is dehydrogenated, at the same selectivity level, than in the prior art processes employing a cocurrent flow direction. Thus, along with a lower amount of cracked gases, the amount of unconverted hydrocarbon feed materials in the product stream is also lowered. Since the recovery of the olefinic products require additional process steps, such as distillation, extraction or other unit operations, separation costs are less expensive the higher the content of the desired product obtained.

BRIEF DESCRIPTION OF THE DRAWINGS

The accompanying drawing represents a typical reactor system which may be employed in this invention. A, B and C refer to three distinct reactors. Each of the reactors is coupled with several valves for controlling the feed hydrocarbons (4A, 4B, 4C), the reduction gas (3A, 3B, 3C), the oxygen containing gas (6A, 6B, 6C), the injection fuel (5A, 5B, 5C), the hydrocarbon products (7A, 7B, 7C) and the oxygen containing gas after combustion (1A, 1B, 1C).

For ease of illustration, a description of the reaction phase of reactor A will now be discussed.

Before starting the reaction phase for the reactor, the reaction chamber is evacuated by a vacuum pump (line 11). For this purpose the valve 2A is opened. All other valves 1A, 3A–7A are closed. In this case the regeneration line 13 is used for evacuation. An alternative is to use the product line 12 at valve (8A) instead of the regeneration line 13. In this alternative, the vacuum pump is connected with line 9.

At the beginning of the reaction phase, valve 2A is closed, or valve (8A) alternatively, and valves 4A and 7A are opened. The hydrocarbon feed flows through line 10 into the reactor and the reaction products leave the reactor using line 12.

For safety reasons, purging and evacuation are necessary before starting the regeneration phase. The purge stream uses the hydrocarbon lines 10 and 12. Additional valves which are not included in the figure control the purge gas and the effluent. The evacuation is achieved by using the vacuum line 11 or 9 alternatively.

The oxygen containing gas is fed by line 14 through the opened valve 6A into the reactor A. In the reaction chamber the coke is burnt off by the gas and the effluent leaves the reactor through the opened valve 1A by line 13.

The rest of the valves at the reactor A are closed. During combustion the gas stream is in a direction opposite to that of the reaction phase, as shown in the figure.

For increasing the temperature in the reactor it might be useful to inject fuel gas into the oxygen containing gas by line 15 through the opened valve 5A. This alternative permits the introduction of increased heat into the catalyst bed. After evacuation by using the corresponding lines and valves the chromium of the catalyst is reduced by hydrogen which is fed through line 16 and the opened valve 3A into the reactor. For its outlet the hydrocarbon product line 12 is used.

DETAILED DESCRIPTION OF THE PREFERRED EMBODIMENTS

The hydrocarbons dehydrogenated by the process of this invention can be any alkane or monoolefin. Short chain hydrocarbons having two to six carbon atoms are especially preferred. In particular, the hydrocarbon feedstock may include propane, n-butane, n-pentane, isomeric butanes and pentanes, and mixtures of at least two of these saturated hydrocarbons. Furthermore, the feedstock may contain considerable amounts of olefinic byproducts such as propene, butadiene, pentadiene and the various butenes and pentenes. These olefinic byproducts are recycled from the product stream following the dehydrogenation of the original feedstock.

The hydrocarbons, either pure or diluted with an inert gas, are passed adiabatically through the fixed bed reactor. The reactor system employed may contain a single reactor or a multitude of reactors. In a single reactor scheme, each reactor sees the periodical changes in the hydrocarbon feed and product flow, the amount of material in vessels and towers, etc. When two reactors are employed, one reactor may be employed for the reaction cycle and the other for the regeneration cycle. Periodical flow and hold-up changes can therefore be minimized. The feed stream to the two reactor system is continuous. In the reactor system wherein more than two reactors are employed, the reaction and generation cycles are appropriately overlapped. The fixed bed reactor illustrated in FIG. 1 contains three distinct reactors. Alternatively, in this invention, fixed bed reactors arranged in parallel may also be employed. Commercially, it is preferable to employ at least two reactors in parallel. While each reactor is operated discontinuously, they generate a continuous product stream.

The dehydrogenation catalysts are comprised of alumina. Metallic materials such as, e.g., chromic oxide (also means "chromium oxide") or platinum may be employed with the alumina. These metals are applied to the alumina by impregnating the alumina with aqueous solutions of the corresponding salts or by precipitation.

The oxygen-containing gas is either a mixture of air and flue gases or air and nitrogen. The oxygen content in the gas is between 2 to 20 wt. %. The gas may also include 0 to 18 wt. % water, 0 to 30 wt. % carbon dioxide, 50 to 98 wt. % nitrogen and less than 1% of such contaminants as carbon monoxide, sulfur dioxide and nitrogen oxides. An injection fuel may be employed in combination with the oxygen-containing gas.

The hydrocarbon feed mixture is fed into the fixed bed reactor containing the dehydrogenation catalyst at a rate between 0.2 to 10 liquid volume of feed per volume of catalyst per hour. The hydrocarbon feed mixture prior to entry into the catalyst bed is between 500° to 680° C. (930° C. to 1260° F.). The temperature at the entry of the reactor for the hydrocarbon feed is between 540° to 700° C. (1000° to 1320° F.).

The dehydrogenation and regeneration cycles last between one minute to one hour. During the dehydrogenation cycle, a temperature drop is established in the reactor. Further, since the cooling of the regeneration gas is in a direction opposite to that of the flow direction of the hydrocarbon feed, a lower temperature prevails at the place of entry of the hydrocarbons in the catalyst bed than at the exit point of the hydrocarbons. The temperature at the exit of the reactor for the hydrocarbon feed is between 500° C. to 660° C. (930° to 1220° F.). The temperature drop in the catalyst bed after regeneration is between 0 to 160° C. (0° to 290° F.). The temperature of the fixed catalyst bed can be controlled by varying the amount and temperature of the regeneration mixture. Further, the composition of the oxygen-containing gas can also control the bed temperature, e.g., oxygen content and amount of injection fuel, if added. Thus, the newly fed reaction gas encounters a temperature optimal for the reaction process. As the hydrocarbon mixture flows through the fixed bed, the increasing catalyst temperature and the decreasing temperature of the reaction gas (which decreases as the reaction progresses) mutually compensate one another. As a result, on a time-averaged basis, the reaction proceeds at a temperature such that the conversion and selectivity of the reaction are maintained at a high level.

The conversion range i.e., the dehydrogenation of the feedstock, is between 10 to 85% by wt., preferably between 40 to 70% by weight. The selectivity range of the alkene produced is between 80 to 98% by mole. At the preferred conversion range, the selectivity range is between 85 to 96% by mole. Under such conditions, the yields range from 10 to 70% mol, preferably between 35 to 60% mol.

The olefins, particularly the short chain olefins, produced by this process may be ultimately used in various facets of technology, such as in the alkylation of hydrocarbons or in the production of ethers from alcohols, which, in turn, are valuable additives in the production of high octane carburetor fuels. Further, the butadiene obtained in the dehydrogenation of butene may be used in the production of synthetic rubber.

The present invention will be illustrated by certain examples which are provided for purposes of illustration only and are not intended to limit the invention.

EXAMPLE 1

The catalyst was produced by impregnating alumina with chromium nitrate, drying, and calcining. The catalyst contained 17.4 wt. % of chromic oxide. The alumina employed was ordinary commercial gamma-alumina, obtained from the firm Harshaw. A chromium oxide catalyst and a hydrocarbon mixture, comprising 1.08 wt. % propane, 98.11 wt. % isobutane, 0.40 wt. % n-butane, 0.13 wt. % 1-butene and 0.28 wt. % isobutene, and an oxygen-containing gas containing 16 and 84 wt. % of oxygen and nitrogen, respectively, were passed in alternation through a tubular reactor 40 mm diameter × 300 mm long.

The reactor was operated to provide a dehydrogenation reaction phase of 9 min and a regeneration phase of 18 min total, in alternation. In the regeneration phase, the reactor was purged 2 min with nitrogen before the coke was burned off, and after the coke burning the reactor was evacuated for 2 min. In the dehydrogenation phase, the stated hydrocarbon mixture was fed at the rate of 0.5 wt. parts per hr. per wt. part catalyst. The hydrocarbon mixture was heated by a preheater to 630° C. at its entrance to the catalyst bed. During the regeneration phase a temperature drop of 60° C. was established in the catalyst bed by passing the oxygen-containing gas, heated to 640° C. through the reactor in the direction opposite the flow direction of the hydrocarbons, whereby a temperature of 580° C. was established at the entry (plane) of the hydrocarbon feed into the catalyst bed and 640° C. at the exit of the hydrocarbon.

The products leaving the reactor (hydrocarbons during the reaction phase, and $CO_2$-containing gaseous combustion products during the regeneration phase) were collected and were analyzed on a gas chromatograph. The total conversion of the isobutane and the selectivity of the conversion to isobutene were determined.

Under the above conditions the conversion of isobutane was 66.8 mol %, the selectivity for isobutene was 91.3 mol %, and the yield of isobutene was, accordingly, 61 mol %.

COMPARATIVE EXAMPLE 1

The method described in Example 1 was carried out except that the oxygen-containing gas heated to 640° C. and the hydrocarbon mixture heated to 630° C. were passed through the reactor in the same flow direction, whereby a temperature gradient was established wherewith the temperature at the inlet plane of the hydrocarbon feed into the catalyst bed was 640° C., and that at the exit plane from the catalyst bed was 580° C.

Under these conditions, the conversion of isobutane was only 60.3 mol %, the selectivity for isobutene was 91.8 mol %, and the yield of isobutene was, accordingly, only 55.4 mol %.

Having now fully described this invention, it will be apparent to one of ordinary skill in the art that many changes and modifications can be made thereto without departing from the spirit or scope of the invention as set forth herein.

What is claimed as new and desired to be secured by letter patent of the United States is:

1. A method for producing unsaturated or polyunsaturated hydrocarbons, comprising in order the following steps:
    (a) adiabatically passing through at least one fixed catalyst bed reactor a hydrocarbon feed mixture selected from the group consisting of saturated alkanes and monoolefins;
    (b) recovering said unsaturated or polyunsaturated hydrocarbons from the effluent of said adiabatically passing step;
    (c) purging said catalyst bed;
    (d) passing an oxygen-containing gas which has been preheated to a temperature greater than the temperature of said catalyst bed, through the catalyst bed in a direction opposite to that of said hydrocarbon feed mixture;
    (e) evacuating said catalyst bed.

2. The method of claim 1 wherein said saturated alkanes and monoolefins of said hydrocarbon feed mixture contain two to six carbon atoms.

3. The method of claim 1 wherein said hydrocarbon feed mixture is adiabatically passed through at least two fixed catalyst bed reactors which are arranged in parallel.

4. The method of claim 1 wherein said oxygen-containing gas contains 50 to 98 wt. % nitrogen.

5. The method of claim 1 wherein said hydrocarbon feed mixture is heated to 500° to 680° C. prior to passing it through said fixed catalyst bed reactor.

6. A method for producing unsaturated or polyunsaturated hydrocarbons, comprising, in order, the following steps:
   (a) adiabatically passing though at least one fixed catalyst bed reactor a hydrocarbon feed mixture selected from the group consisting of saturated alkanes and monoolefins;
   (b) recovering the said unsaturated or polyunsaturated hydrocarbons from the effluent of the step (a);
   (c) purging the said catalyst bed;
   (d) passing an oxygen-containing gas through the catalyst bed in a direction opposite to that of the said hydrocarbon feed mixture, while controlling the temperature and the composition of the oxygen-containing gas; and
   (e) evacuating the said catalyst.

7. A method for producing unsaturated or polyunsaturated hydrocarbons, comprising:
   (a) adiabatically passing through at least one fixed catalyst bed reactor a hydrocarbon feed mixture selected from the group consisting of saturated alkanes and monoolefins;
   (b) recovering unsaturated or polyunsaturated hydrocarbons from the effluent of step (a);
   (c) purging the catalyst bed; and
   (d) passing an oxygen-containing gas through the catalyst bed in a direction opposite to that of the said hydrocarbon feed mixture while controlling the termperature of the said catalyst bed by varying the temperature or the composition of the said oxygen-containing gas;
   (e) evacuating the said catalyst bed; and
   (f) repeating step (a).

8. A method of producing unsaturated or polyunsaturated hydrocarbons, comprising, in order, the following steps;
   (a) adiabatically passing through at least one fixed catalyst bed reactor a hydrocarbon feed mixture selected from the group consisting of saturated alkanes and monoolefins;
   (b) recovering the said saturated or polyunsaturated hydrocarbons from the effluent of step (a);
   (c) purging the said catalyst bed;
   (d) passing an oxygen-containing gas through the catalyst bed in a direction opposite to that of the said hydrocarbon feed mixture, while controlling the temperature of the said catalyst bed by varying the composition or the temperature of the oxygen-containing gas; and
   (e) evacuating the said catalyst.

* * * * *